United States Patent [19]

Chiusoli et al.

[11] 4,355,168

[45] Oct. 19, 1982

[54] PROCESS FOR PREPARING ARYL- OR HETEROARYLHEXADIENOIC ACIDS

[75] Inventors: Gian P. Chiusoli, Parma; William Giroldini, Bibbiano; Luciano Pallini, Fornovo Taro; Giuseppe Salerno, Parma, all of Italy

[73] Assignee: Montedison S.p.A., Milan, Italy

[21] Appl. No.: 212,238

[22] Filed: Dec. 2, 1980

[30] Foreign Application Priority Data

Dec. 3, 1979 [IT] Italy ................. 27789 A/79

[51] Int. Cl.$^3$ .................. C07D 213/55; C07D 333/24; C07C 57/42; C07C 51/347
[52] U.S. Cl. .................................... 546/341; 546/301; 546/318; 546/326; 549/66; 549/71; 549/79; 549/471; 562/471; 562/495; 562/496
[58] Field of Search ....................... 562/496, 495, 471; 546/341, 301, 318, 326; 549/79, 66, 71; 260/346.22

[56] References Cited

U.S. PATENT DOCUMENTS

| | | | |
|---|---|---|---|
| 4,011,339 | 3/1977 | Galantay et al. | 424/317 |
| 4,219,659 | 8/1980 | Fujisawa et al. | 549/79 |
| 4,221,915 | 9/1980 | Kondo et al. | 549/78 |

FOREIGN PATENT DOCUMENTS 32548  7/1981  European Pat. Off. ............ 562/496

*Primary Examiner*—Alan L. Rotman

[57] ABSTRACT

There is disclosed and claimed a process for preparing aryl- and heteroarylhexadienoic acids which is characterized in that an aryl- or heteroarylacetylene having the formula: R—C≡CH, wherein R is an aryl or heteroaryl group, optionally substituted and having in the aggregate up to 20 carbon atoms, is reacted with 3-butenoic acid $CH_2=CH—CH_2—COOH$, in an alcoholic medium, at temperatures maintained between 50° C. and 120° C., approximately, in the presence of a catalyst selected from among the phosphinic complexes of rhodium having the formulas: III, $Rh(PR'_3)_nL_mX$ associated with alkaline salts of carboxylic acids having up to 4 carbon atoms, and IV, $Rh(PR'_3)_nL_p{}^+Y^-$, wherein R' is a hydrocarbyl group having up to 12 carbon atoms; "L" is a linear or cyclic olefin selected from among the olefins having from 2 to 10 carbon atoms and the chelating olefins having from 6 to 8 carbon atoms, n is an integer from 1 to 3, m is an integer from 0 to 2 and such that n+m=2 or 3, and p is an integer from 0 to 3 and such that n+p=3 or 4; X is an anion selected from among the haloid anions, preferably the hydrochloric anion, and the anions of carboxylic acids having up to 4 carbon atoms and Y is a sparingly coordinating anion, preferably selected from $PF_6{}^-$ and $BF_4{}^-$.

The compounds obtained are used as intermediates for organic syntheses, with particular regard to the so-called "fine chemicals" such as, for example, additives for polymers and paints, plasticizers, and the like.

14 Claims, No Drawings

PROCESS FOR PREPARING ARYL- OR HETEROARYLHEXADIENOIC ACIDS

BACKGROUND OF THE INVENTION

As far as applicants know, the reaction on which the process of the present invention is based has never been described or suggested by the prior art.

According to the art—however through reactions not related to the one of this invention—3,5-dienoic acids and substituted derivatives thereof can be prepared by means of alternative processes based on the Witting synthesis starting from aldehydes and organic phosphorous compounds in stoichiometric amounts.

Nevertheless, techniques of such type require a preliminary preparation of suitable aldehydes, which are sometimes difficult to prepare or retrieve and the stoichiometric use of phosphorated intermediates, which are objectionable from the viewpoint of the compatibility of the effluents with the present environmental protection requirements and with the financial burden connected thereto, which render such techniques substantially non-applicable on an industrial scale.

Finally, catalytic processes are known, which are useful to prepare 3,5-dienoic acids, optionally aryl-substituted, by reaction of substituted allyl halides with acetylene and carbon monoxide in hydroxylated solvents in the presence of nickel carbonyl or precursors thereof, followed by isomerization.

Said methods are of minor industrial importance due to the use of nickel carbonyl derivatives and of carbon monoxide. Furthermore, they are not suitable for industrial applications owing to the high toxicity of the described conditions.

THE PRESENT INVENTION

It is an object of this invention to provide a simple and economic process for preparing aryl- or heteroarylhexadienoic acids, free from the drawbacks cited with regard to the prior art.

This, and other objects which will be apparent to a technician skilled in the art from the following description, are achieved, according to the present invention, by a process for preparing aryl- and heteroarylhexadienoic acids, characterized in that an aryl- or heteroarylacetylene of formula:

$$R-C\equiv CH \quad (I)$$

where R is an aryl or heteroaryl group, optionally substituted, having up to 20 carbon atoms in the aggregate, is reacted with 3-butenoic acid of formula:

$$CH_2=CH-CH_2-COOH \quad (II)$$

in an alcoholic medium and in an inert atmosphere, in the presence of a catalyst selected from among the phosphinic complexes of rhodium defined in more detail hereinafter, at temperatures approximately maintained between 50° C. and 120° C.

The reaction can be represented by the following equation

$$RC\equiv CH + CH_2=CHCH_2-COOH \xrightarrow{\text{Rh cat. (complex)}} \quad (1)$$
$$RCH=CH-CH=CH-CH_2-COOH.$$

The reaction occurs in like manner also for the other possible aryl- and heteroarylhexadienoic acids.

In the equation, R has the meaning specified hereinabove.

The reaction is conducted in an organic alcoholic solvent, either alone or in admixture with minor amounts, up to 20% by weight of water. Aliphatic alcohols having up to 5 carbon atoms have proved to be suitable solvents, the presently preferred solvent being ethyl alcohol.

The reaction temperature is comprised, as mentioned hereinbefore, between 50° C. and 120° C., approximately.

The catalyst is selected from the complexes of monovalent rhodium with hydrocarbyl phosphines having the formulas:

$$Rh(PR'_3)_n L_m X \quad (III)$$

associated with alkaline salts of carboxylic acids having up to 4 carbon atoms, and

$$Rh(PR'_3)_n L_p^+ Y^- \quad (IV)$$

in which
- R' is a hydrocarbyl group having up to 12 carbon atoms;
- L is a linear or cyclic olefin having 2 to 10 carbon atoms or a chelating olefin having 6 to 8 carbon atoms;
- n is an integer selected from 1 to 3,
- m is an integer selected from 0 to 2 and such that n+m=2 or 3,
- p is an integer from 0 to 3 and such that n+p=3 or 4;
- X is an anion selected from the haloid anions, preferably the hydrochloric anion, and the anions of carboxylic acids having up to 4 carbon atoms,
- Y is selected from $BF_4^-$ and $PF_6^-$.

Generally, it is possible to use sparingly coordinating Y anions.

Said Rh complexes are known in themselves and commercially available, or they are obtained according to conventional methods, for example by reduction of rhodium salts in the presence of a binder (phosphine), etc. The preparation can be also effected "in situ".

In any case, it is possible to operate also in the presence of an excess of phosphinic binder $PR'_3$.

In particular, effective results have been obtained by using complexes in which R' is selected from butyl, phenyl, anisyl; the olefin is selected from ethylene, cyclooctene and norbornene or, if a chelating olefin is used, 1,5-hexadiene, 1,5-cyclooctadiene and norbornadiene.

Of the starting materials, the 3-butenoic acid (II) is a compound industrially known as an intermediate. The aryl- and heteroarylacetylenes (I), are known too, and can be prepared according to known or conventional techniques.

Phenylacetylene, methoxyphenylacetylene, pyridylacetylene, thienylacetylene, benzofurylacetylene, etc., have proved to be effective aryl- and heteroarylacetylenes (I).

As explained hereinabove, the aryl- or heteroarylacetylene (I) can consist of an acetylene derivative $R-C\equiv CH$ in which R is an aryl or a heteroaryl, optionally substituted, having up to 20 carbon atoms, the only condition regulating the choice of which is that it must be inert under the reaction condition.

Therefore, it is possible to employ acetylenes RC≡CH in which R is a benzene, a naphthalene, an anthracene, etc., or a heterocyclic radical, i.e., containing "hetero" atoms in the cycle such as O, N, S, for example the thienyl radical, the benzofuran radical, etc.

Radicals R as defined herein can be also substituted, in their turn, by alkyl, alkoxyl, carbalkoxyl groups having 1 to 4 carbon atoms, by halogens, etc., and in general, as indicated herein, by groups not interfering with the reaction trend.

Among the catalysts, $RhCl(PPh_3)_3$ and $[Rh(cyclooctadiene)(PPh_3)_2]^+PF_6^-$ are particularly effective.

The reagents are employed according to substantially stoichiometric molar ratios, while their concentration in the solvent is not critical for the purposes of the reaction.

The reaction, as explained hereinabove, is catalytic; catalyst amounts of the order of at least 0.01 millimoles per liter of the reacting mixture are sufficient, but the amount may be higher, up to about 100 millimoles per liter.

When catalysts of the type covered by formula (III) are utilized, the reaction is conducted in the presence of alkaline salts, of Na or K, of organic acids such as acetic acid or the 3-butenoic acid itself. The amounts are in excess in respect of the catalyst (III), ranging from 2 to 200 moles. If 3-butenoate of Na or K is used, it is sufficient to neutralize the 3-butenoic acid subjected to reaction with NaOH or KOH.

The reaction is carried out under an inert atmosphere, such as a nitrogen or argon atmosphere.

The obtained product is separated according to conventional techniques by acidification ($H_2SO_4$) after distillation of the solvent, extraction, etc.

The products consist prevailingly of stereoisomers, usually 4, of the acids, for example of 6-phenyl-3,5-hexadienoic acid.

A selectivity for one of the possible isomers can be attained by using catalysts of type (IV).

The reaction times vary depending on the nature of the acetylene compound, of the catalyst and of the other reaction parameters.

The presently preferred embodiment of the process of this invention is conducted as follows:

The catalyst complex, the 3-butenoic acid, the aryl- or hetero-arylacetylene (I), the alkaline salt, if any, and then the selected solvent are introduced into a closed reactor, in a nitrogen atmosphere at atmospheric pressure. The resulting solution is kept at the selected temperature as long as necessary.

The mixture is then treated with a dilute inorganic acid; the organic layer is separated by extraction with the solvent (ethyl ether).

By treating the organic extract with aqueous $Na_2CO_3$ and by successively acidifying and extracting again the new aqueous phase, the acid portion separates, from which the acids, in their turn, are separated by distillation, etc.

The process, thanks to the mild operating conditions, appears as particularly advantageous for commercial use.

Further advantages consist in the availability of the starting compounds and in the selectivity of the reaction.

Furthermore, rhodium can be further utilized for other catalytic cycles.

Finally, the reaction is conducted with two reagents only, without using gaseous phases and conditions causing environmental pollutions, etc., such as the use of nickel carbonyl, etc.

The invention is described more specifically in the following examples, which are given, however, for merely illustrative purposes.

Example 1 comprises also the isomerization of the mixture of the four isomers obtained, namely of the 6-phenyl-3,5-hexadienoic isomers to the type trans-trans. Ph means phenyl.

EXAMPLE 1

0.1 g of $RhCl(PPh_3)_3$ and 0.8 g of potassium acetate were introduced, in a nitrogen atmosphere, into a 50-ml flask. 34 ml of deaerated ethyl alcohol at 95% were then added, and successively 1.1 g of phenylacetylene as well as 1.15 g of 3-butenoic acid. The mixture was heated to 80° C. in a water bath. A homogeneous dark orange solution formed, which was kept at 80° C. for 24 hours.

The reaction mass was allowed to cool down, and after removal of the ethyl alcohol under vacuum, it was acidified with dilute sulphuric acid and extracted with ethyl ether. The ether extract was treated with water and sodium bicarbonate to obtain the acid portion in the form of an alkaline salt. Such acid portion was released with dilute mineral acid (HCl): it prevailingly contained the mixture of stereoisomers of the 6-phenyl-3,5-hexadienoic acid and the unconverted 3-butenoic acid, which was recovered by distillation under high vacuum at room temperature. The resulting phenyl-hexadienoic acids, after purification on silica gel, weighed 0.91 g, corresponding to a yield of 45% in respect of the fed phenylacetylene. The catalyst activity corresponded to 45 moles of product per mole of rhodium complex.

The mixture of the phenylhexadienoic acids so obtained, after treatment with hot concentrated caustic soda, essentially led to the sodium salt of the trans-trans 6-phenyl-3,5-hexadienoic acid.

EXAMPLE 2

Under the same conditions as in Example 1, 0.12 g of $[Rh(cyclooctadiene)(PPh_3)_2]^+PF_6^-$ and 0.14 g of $PPh_3$ were reacted. 40.0 ml of ethyl alcohol at 95%, 1.4 g of 3-butenoic acid and 1.4 g of phenylacetylene were added, whereupon the mass was heated to 80° C. for 48 hours.

By operating according to the preceding example, a mixture of 6-phenyl-3,5-hexadienoic acids containing predominantly ($\geq 75\%$) the 3-trans-5-cis isomer was obtained, the catalyst activity being equal to 40 moles per mole of complex.

EXAMPLE 3

Following the modalities and conditions of Example 1, a corresponding amount of p-methoxyphenylacetylene was reacted. After treatment analogous to Example 1, the mixture of the 4 isomers of the 6-p-methoxyphenyl-3,5-hexadienoic acid was obtained.

EXAMPLE 4

Operating according to the same modalities and conditions as in Example 1, a corresponding amount of 2-ethynylthiophene was reacted. After an analogous treatment, the mixture of the 4 isomers of the 6-(2-thienyl)-3,5-hexadienoic acid was obtained, the catalyst activity being equal to 38 moles per mole of complex.

We claim:

1. A process for preparing aryl- or heteroarylhexadienoic acids, characterized in that an aryl- or heteroarylacetylene of formula: R—C≡CH (I), wherein R is an aryl group containing 1 or 2 rings or a heteroaryl group containing 1 or 2 rings and 1 to 2 heteroatoms selected from O, N, and S, in the radical, optionally substituted by substituents inert under the reaction conditions, and selected from halogen and alkyl, alkoxyl and carboalkoxy groups containing from 1 to 4 carbon atoms said aryl or heteroaryl acetylene containing a total of up to 20 carbon atoms, is reacted with 3-butenoic acid $CH_2=CH—CH_2—COOH$ (II), in an alcoholic medium and in an inert atmosphere, at a temperature approximately maintained between 50° C. and 120° C., at atmospheric pressure, in the presence of a catalyst selected from the group consisting of the phosphinic complexes of rhodium having the formulas: $Rh(PR'_3)_nL_mX$ (III) associated with alkaline salts of carboxylic acids having up to 4 carbon atoms, and $Rh(PR'_3)_nL_p{}^+Y^-$ (IV) wherein R' is a hydrocarbyl group having up to 12 carbon atoms; L is a linear or cyclic olefin selected from the olefins having a number of carbon atoms of from 2 to 10 and the chelating olefins having 6 to 8 carbon atoms, n is an integer from 1 to 3, m is an integer from 0 to 2 and such that n+m=2 or 3, and p is an integer from 0 to 3 and such that n+p=3 or 4; X is an anion selected from the haloid anions and the anions of carboxylic acids having up to 4 carbon atoms, and Y is a sparingly coordinating anion.

2. The process of claim 1 in which the anion X is the hydrochloric anion.

3. The process of claim 1 in which the sparingly coordinating anion Y is $PF_6^-$ or $BF_4^-$.

4. The process of claim 1, in which the alcoholic medium is an aliphatic alcohol having up to 5 carbon atoms.

5. The process of claim 4, in which the alcoholic medium is ethyl alcohol.

6. The process of claim 4 or 5, in which the alcoholic medium is employed in association with up to about 20% by weight of water.

7. The process of claim 1, in which the rhodium catalyst is a complex with a phosphine $PR'_3$ in which R' is selected from the group consisting of butyl, phenyl, and anisyl, and the olefin is selected from the group consisting of ethylene, cyclooctene, norbornene, 1,5-hexadiene, 1,5-cyclooctadiene and norbornadiene.

8. The process of claim 1, in which the aryl- or heteroarylacetylene is selected from the group consisting of phenylacetylene, methoxyphenylacetylene, pyridylacetylene, thienylacetylene and benzofurylacetylene.

9. The process of claim 1, in which the catalyst is selected from the group consisting of $RhCl(PPh_3)_3$ and $[Rh (cyclooctadiene) (PPh_3)_2]^+PF_6^-$.

10. The process of claim 1, in which the aryl- or heteroarylacetylene and the 3-butenoic acid are reacted in substantially equimolar ratios.

11. The process of claim 1, in which the rhodium complex catalyst is employed in amounts from at least equal to 0.01 millimoles per liter of reacting mixture up to about 100 millimoles per liter.

12. The process of claim 1, in which the reaction is conducted in the presence of an excess of phosphinic binder $PR'_3$, wherein R' is a hydrocarbyl group having up to 12 carbon atoms.

13. The process of claim 1, in which the alkaline salt of the carboxylic acid associated with the catalyst of formula (III) is selected from the group consisting of sodium acetate, potassium acetate, and the sodium or potassium salt of the 3-butenoic acid.

14. The process of claim 13, in which the alkaline salt of the carboxylic acid is employed in an excess approximately comprised between 2 and 200 moles in respect of the catalyst of formula (III).

* * * * *